US011110206B2

(12) United States Patent
Leite De Almeida Monteiro De Oliveira et al.

(10) Patent No.: US 11,110,206 B2
(45) Date of Patent: Sep. 7, 2021

(54) SILK SERICIN-BASED HYDROGEL, METHODS AND USES THEREOF

(71) Applicant: UNIVERSIDADE CATÓLICA PORTUGUESA, Oporto (PT)

(72) Inventors: Ana Leite De Almeida Monteiro De Oliveira, Matosinhos (PT); Sara Isabel Macedo Baptista Da Silva, Vila Nova de Gaia (PT); Sandra Cristina Ferreira Borges, Matosinhos (PT); Paulo Jorge Pereira Alves, Gondomar (PT)

(73) Assignee: UNIVERSIDADE CATÓLICA PORTUGUESA, Oporto (PT)

( * ) Notice: Subject to any disclaimer, the term of this patent is extended or adjusted under 35 U.S.C. 154(b) by 132 days.

(21) Appl. No.: 16/317,051

(22) PCT Filed: Jul. 12, 2017

(86) PCT No.: PCT/IB2017/054211
§ 371 (c)(1),
(2) Date: Jan. 11, 2019

(87) PCT Pub. No.: WO2018/011732
PCT Pub. Date: Jan. 18, 2018

(65) Prior Publication Data
US 2019/0224374 A1    Jul. 25, 2019

(30) Foreign Application Priority Data

Jul. 12, 2016  (PT) ........................................ 109525

(51) Int. Cl.
| A61L 27/52 | (2006.01) |
| A61L 27/54 | (2006.01) |
| C08J 3/075 | (2006.01) |
| A61L 15/48 | (2006.01) |
| A61L 15/58 | (2006.01) |
| A61L 15/44 | (2006.01) |
| A61L 15/60 | (2006.01) |
| A61L 26/00 | (2006.01) |
| A61L 27/22 | (2006.01) |
| A61L 15/64 | (2006.01) |

(52) U.S. Cl.
CPC .............. *A61L 27/52* (2013.01); *A61L 15/44* (2013.01); *A61L 15/48* (2013.01); *A61L 15/58* (2013.01); *A61L 15/60* (2013.01); *A61L 15/64* (2013.01); *A61L 26/008* (2013.01); *A61L 26/0047* (2013.01); *A61L 26/0066* (2013.01); *A61L 27/227* (2013.01); *A61L 27/54* (2013.01); *C08J 3/075* (2013.01); *A61L 2300/102* (2013.01); *A61L 2300/204* (2013.01); *A61L 2300/232* (2013.01); *A61L 2300/254* (2013.01); *A61L 2300/406* (2013.01); *A61L 2300/42* (2013.01); *A61L 2300/802* (2013.01); *A61L 2400/04* (2013.01); *A61L 2400/06* (2013.01); *A61L 2430/06* (2013.01); *A61L 2430/24* (2013.01); *A61L 2430/34* (2013.01); *C08J 2389/00* (2013.01)

(58) Field of Classification Search
CPC ........ A61L 27/52; A61L 15/58; A61L 26/008; A61L 26/0047; A61L 27/227; A61L 27/54; A61L 2300/102; A61L 2300/204; A61L 2300/232; A61L 2300/254; A61L 2300/406; A61L 2300/42; A61L 2300/802; A61L 2400/06; C08J 3/075
See application file for complete search history.

(56) References Cited

U.S. PATENT DOCUMENTS

2016/0136241 A1    5/2016  Wang et al.

FOREIGN PATENT DOCUMENTS

| CN | 106750395 A | 5/2017 |
| WO | 2015054125 A1 | 4/2015 |

OTHER PUBLICATIONS

Anghileri et al., Journal of Biotechnology, 2007, vol. 127, p. 508-519.*
Partlow et al., Adv. Funct. Mater. 2014, vol. 24, pp. 4615-4624, and Supporting material pp. 1-6.*
Aljawish et al. "Enzymatic synthesis of chitosan derivatives and their potential applications." Journal of Molecular Catalysis B: Enzymatic 112 (2015): 25-39.
Almeida et al. "New biotextiles for tissue engineering: Development, characterization and in vitro cellular viability." Acta biomaterialia 9.9 (2013): 8167-8181.
Aramwit et al. "Potential applications of silk sericin, a natural protein from textile industry by-products." Waste Management & Research. Epub (2011) doi: 1177/0734242X11404733. 9 pages.
Atala. "Regenerative Medicine Strategies." Journal of Pediatric Surgery (2012) 47, 17-28.
Berardesca et al. "Randomized, double-blinded, vehicle-controlled, split-face study to evaluate the effects of topical application of a Gold Silk Sericin/Niacinamide/Signaline complex on biophysical parameters related to skin ageing." International Journal of Cosmetic Science 37.6 (2015): 606-612.

(Continued)

*Primary Examiner* — Kade Ariani
(74) *Attorney, Agent, or Firm* — Leason Ellis LLP

(57) ABSTRACT

The present disclosure relates to a novel sericin-based hydrogel wherein the silk sericin is enzymatically cross-linked for an improved treatment of wound healing, ischemic diseases or cardiovascular diseases, namely chronic wound healing, in particular diabetic wound.

18 Claims, 12 Drawing Sheets

(56) References Cited

OTHER PUBLICATIONS

Boateng et al. "Composite alginate and gelatin based bio-polymeric wafers containing silver sulfadiazine for wound healing." International Journal of Biological Macromolecules 79 (2015): 63-71.

Catanzano et al. "Alginate-hyaluronan composite hydrogels accelerate wound healing process." Carbohydrate Polymers 131 (2015): 407-414.

Chen et al. "A novel nanocomposite for bone tissue engineering based on chitosan-silk sericin/hydroxyapatite: biomimetic synthesis and its cytocompatibility." RSC Advances 5.69 (2015): 56410-56422.

Chlapanidas et al. "Sericins exhibit ROS-scavenging, anti-tyrosinase, anti-elastase, and in vitro immunomodulatory activities." International Journal of Biological Macromolecules 58 (2013): 47-56.

Dhivya et al. "Wound dressings—a review." BioMedicine 5.4 (2015): 24-28.

Fan et al. "Preparation and characterization of chitosan/gelatin/PVA hydrogel for wound dressings." Carbohydrate polymers 146 (2016): 427-434.

Frykberg et al. "Diabetic foot disorders: a clinical practice guideline (2006 revision)." The Journal of Foot and Ankle Surgery 45.5 (2006): S1-S66.

Gainza et al. "Advances in drug delivery systems (DDSs) to release growth factors for wound healing and skin regeneration." Nanomedicine: Nanotechnology, Biology and Medicine 11.6 (2015): 1551-1573.

Hurd. "Understanding the financial benefits of optimising wellbeing in patients living with a wound." Wounds International 4.2 (2013): 13-7.

Jin et al. "Influence of hydrophilic polymers on functional properties and wound healing efficacy of hydrocolloid based wound dressings." International Journal of Pharmaceutics 501.1-2 (2016): 160-166.

Kaur et al. "Photoprotection by silk cocoons." Biomacromolecules 14.10 (2013): 3660-3667.

Khampieng et al. "Silk sericin loaded alginate nanoparticles: preparation and anti-inflammatory efficacy." International Journal of Biological Macromolecules 80 (2015): 636-643.

Kundu et al. "Silk sericin/polyacrylamide in situ forming hydrogels for dermal reconstruction." Biomaterials 33.30 (2012): 7456-7467.

MacDonald et al. Editors. "Wound and Lymphoedema Management." World Health Organization. 2010. France. 136 pages.

Mahmoud et al. "Norfloxacin-loaded collagen/chitosan scaffolds for skin reconstruction: Preparation, evaluation and in-vivo wound healing assessment." European Journal of Pharmaceutical Sciences 83 (2016): 155-165.

Moreo "Understanding and overcoming the challenges of effective case management for patients with chronic wounds." The Case Manager 16.2 (2005): 62-63, 67.

Morikawa et al. "Rat islet culture in serum-free medium containing silk protein sericin." Journal of Hepato-Biliary-Pancreatic Surgery 16.2 (2009): 223-228.

Nishida et al. "Sustained-release of protein from biodegradable sericin film, gel and sponge." International journal of pharmaceutics 407.1-2 (2011): 44-52.

Ohnishi et al. "Effect of the silk protein sericin on cryopreserved rat islets." Journal of Hepato-Biliary-Pancreatic Sciences 19.4 (2012): 354-360.

Petrie et al. "Gene Therapy in Wound Healing." Surg. Clin. N Am. 83 (2003). 597-616.

Phillips et al. "Estimating the costs associated with the management of patients with chronic wounds using linked routine data." International Wound Journal. ISSN 1742/4801. 13.6 (2015): 1193-1197.

Rahimi et al. "A low-cost flexible pH sensor array for wound assessment." Sensors and Actuators B: Chemical 229 (2016): 609-617.

Ramos et al. "Effect of whey protein purity and glycerol content upon physical properties of edible films manufactured therefrom." Food Hydrocolloids 30.1 (2013): 110-122.

Ribeiro et al. "Influence of different surface modification treatments on silk biotextiles for tissue engineering applications." Journal of Biomedical Materials Research Part B: Applied Biomaterials 104.3 (2016): 496-507.

Sen et al. "Human skin wounds: a major and snowballing threat to public health and the economy." Wound Repair and Regeneration 17.6 (2009): 763-771.

Shi et al. "A novel poly (γ-glutamic acid)/silk-sericin hydrogel for wound dressing: Synthesis, characterization and biological evaluation." Materials Science and Engineering: C 48 (2015): 533-540.

Sivaranjani et al. "Synthesize of Titanium dioxide nanoparticles using *Moringa oleifera* leaves and evaluation of wound healing activity." Wound Medicine 12 (2016): 1-5.

Song et al. "An injectable silk sericin hydrogel promotes cardiac functional recovery after ischemic myocardial infarction." Acta Biomaterialia 41 (2016): 210-223.

Wang et al. "Exploring natural silk protein sericin for regenerative medicine: an injectable, photoluminescent, cell-adhesive 3D hydrogel." Scientific Reports 4 (2014): 7064.

Yan et al. "Bilayered silk/silk-nanoCaP scaffolds for osteochondral tissue engineering: in vitro and in vivo assessment of biological performance." Acta Biomaterialia 12 (2015): 227-241.

* cited by examiner

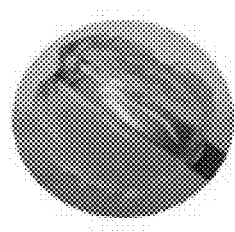
FIG. 3A
L* 74.5 ± 2.7
a* 0.5 ± 0.1
b* 16.7 ± 1.5
FIG. 3B
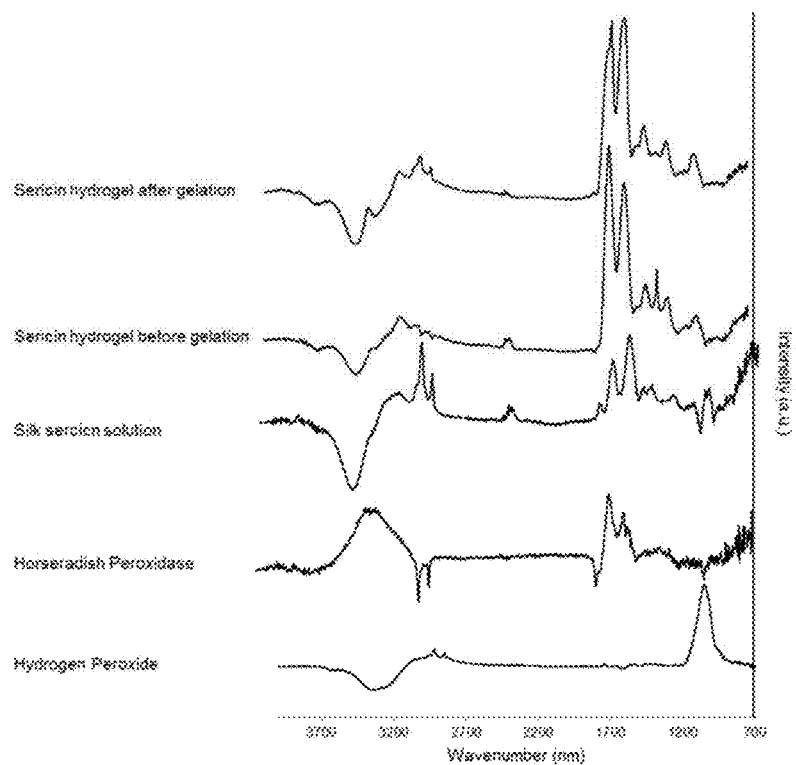
FIG. 3C

SILK SERICIN-BASED HYDROGEL, METHODS AND USES THEREOF

CROSS-REFERENCE TO RELATED PATENT APPLICATIONS

This application is a U.S. National Stage Application under 35 U.S.C. § 371 of International Patent Application No. PCT/IB2017/054211, filed Jul. 12, 2017, which claims the benefit of priority under 35 U.S.C. Section 119(e) of Portuguese Patent Application No. 109525 filed Jul. 12, 2016, both of which are hereby incorporated by reference as if set forth in their respective entireties herein.

TECHNICAL FIELD

The present disclosure relates to a novel sericin-based hydrogel for an improved treatment of wound healing, ischemic diseases or cardiovascular diseases, namely chronic wound healing, in particular diabetic wound.

The present disclosure also relates to an in-situ forming silk sericin-based hydrogel healing bio a novel wound material.

BACKGROUND

A wound means a disruption or injury on the skin structure, integrity and function, leading to the damage of intrinsic skin barriers (1, 2). Common wounds are due to small injuries that may heal quickly, with no required attention and very little discomfort. Nevertheless chronic wounds are defined by the Wound Healing Society as those which have failed to proceed through an orderly and timely reparative process to produce anatomic and functional integrity over a period of 3 months' (3). Chronic wounds may therefore lead to pain, infection and, in severe cases, sepsis, amputation and even death. Besides the physical phenomena wounds can also cause nausea, fatigue, loss of function and mobility and psychological disorders, such as depression, and consequent isolation (4).

Complex wounds can generally be categorized into three types: pressure ulcers, venous leg ulcers, and diabetic foot ulcers (5). In older ages the chronic wounds are more common due to the decrease of the skin's protective layers, placing the patient at greater risk of injury and into further severe complications. Estimating the prevalence of chronic wounds remains difficult, since several wounds do not reach the hospital or medical care services. Different sources suggest that between 5 and 7 million patients in the United States (6) and approximately 18 million patients worldwide suffer from chronic wounds (7). These numbers have turned into one of the major clinical problems worldwide due to the morbidity associated with prolonged periods required for repair and regeneration of the injured tissue, the bleeding, and the risk for infections and septicaemias.

In spite of the current medical advancements, wound healing still remains as an inefficiently managed area and for sure a challenge domain for researchers worldwide. The wound healing process involves four types of stages: haemostasis, inflammation, proliferation and remodelling leading to scar formation. The ultimate goal of wound healing is to have a speedy recovery with minimal scaring (8). The treatment of chronic and complex wounds is a significant burden on the health-care system and on the economy as a whole. Data from 2003 reported in the USA a burden impact over US$1.7 billion on specialty dressings, devices, and topical treatments for chronic wounds. Moreover the annual cost for overall management of these wounds is greater than US$20 billion, not including the additional costs to society in terms of workdays lost or productivity (9).

Currently, there are different types of dressings such as: films/membranes (adherent or non-adherent), hydrogels, hydrocolloids, composite dressings, foams, hydrophilic and hydrophobic fibres, hypertonic, antimicrobial, devices and biologicals (10, 11). The selected dressing must provide an adequately prolonged close contact with the skin area around the wound, absorbing extra secretions exuded from the wound, maintaining moist milieu around the wound, allowing for the air to permeate, ensuring protection, and detaching slickly without causing distress to the wound (10). It is crucial that the clinician understands the function of the dressing in order to maximize the wound bed preparation. The chosen form must be adequate to the area of application, facilitating moisture balance, and preventing infection (10).

Among the different types of dressings, hydrogels comprise a high quantity of water (70%-90%), being suitable for sloughy or necrotic wounds because they maintain the moisture of the wound surface and, simultaneously, the skin hydration (12). Hydrogels have a high permeability to metabolites and have the capability to absorb fluids, providing an ideal environment for wound healing (12). In this regard, growing efforts have been made to study naturally derived biomaterials as hydrogel dressings. Collagen (13), alginates (14), and chitosan (15) are some of the most used systems in the market because of their biocompatibility, biodegradability and similarity to macromolecules recognized by the human body (16). Some examples include: Stimulen™—a collagen gel concentrated dispersion of modified collagens already in amino acid form used to fill wound cavity and Regenecare® Wound Gel with 2% lidocaine which is an alginate hydrogel, indicated for management of pressure ulcers, leg ulcers, cuts and burns (www.woundsource.com).

Among the new generation of natural-based biopolymers being proposed for wound healing and skin regeneration, silk proteins are particularly interesting due to their exceptional properties such as biocompatibility, oxygen and water vapour permeability, enzymatic degradability, processing versatility and the diversity of side chain chemistries available for 'decoration'.

These facts are disclosed in order to illustrate the technical problem addressed by the present disclosure.

GENERAL DESCRIPTION

Chronic wounds are currently a global epidemic and the intervention of specialized wound care emerges as a new era that is about to reform the common wound treatments, which will naturally improve the patient's life value. An ideal dressing should promote the gradual refurbishment of injured tissues in order to advance anatomic and functional integrity. In this sense hydrogels have been widely exploited to bring to the wound bed the moisture and hydration required for the normal re-epithelialization. Up to now, the general methods to prepare silk sericin-based hydrogels have drawbacks such as the long gelation time or harsh preparation conditions, which hold back the application of sericin as a new biomaterial for wound care.

The present disclosure provides a novel route for obtaining a sericin hydrogel within 3 minutes under physiological conditions, via peroxidase mediated cross-linking, allowing for a more efficient clinical application, also improving the wound healing or ischemic diseases treatment and the cell viability. The prepared hydrogels are of mainly amorphous conformation and transparent appearance. The enzymatically cross-linked sericin hydrogels degrade in PBS (pH 7.4) after 17 days, after 7 days in protease IV at biological concentration (3.5 U/mg), and after 4 days under acute and chronic physiological pH values. Additionally, the sericin hydrogels have notable antioxidant activity 0.053±0.002 (eq [Asc. Ac.]g/L), even under physiological protease (3.5 U/mg) degradation. The hydrogels were also able of incorporating cells and support their viability. This disclosure provides a light approach to produce a bio-based hydrogel as an innovative wound treatment, exert an industrial by-product with current environmental damage and neglected biological potential.

Industrially, silk is mostly obtained from the domestic silkworm, *Bombyx mori* being mainly composed by: fibroin (fibrous protein) and sericin (globular protein). Fibroin is a structural protein which constitutes 70% of the silk fibre. It has been extensively studied and used for several biomaterial applications, as revised elsewhere [refs]. Sericin, about 30% of the silk cocoon, is a family of Ser-rich silk proteins that glue fibroin fibres together to form the cocoon. Is a waste by-product of the textile industry since is usually discarded in the degumming wastewater, with environmental consequences (17). Sericin contains 18 kinds of amino acids, mostly polar side chains such as hydroxyl, acidic and basic amino acids, forming a complex of three principal polypeptides with molecular weights of 150 kDa, 180-250 kDa and 400 kDa (18). Although sericin has received much less attention than fibroin, is reported to exhibit several important biological activities such as: biocompatibility, biodegradability, antioxidant behaviour (19), anti-tyrosinase activity (19), UV protective properties (20), moisturizing capabilities (21), cryopreserving effect (22) and serum-free culture medium (23).

As a hydrogel, sericin has been proposed for different biomedical and biotechnological. Sericin has been successfully fabricated and characterized as an a covalently-cross-linked 3D pure sericin-based hydrogel for cell proliferation and drug delivery (24), for cardiac functional recovery after ischemic myocardial infarction (25), as drug delivery system for bone regeneration (26), for in situ dermal reconstruction (27), to promote anti-inflammatory efficacy (28), and has successful hydrogel for wound dressing (29).

The present disclosure relates to novel sericin-based hydrogels, in particular it relates to a novel sericin-based hydrogel prepared for the first time using horseradish peroxidase as an effective crosslinking agent, as a strategy to develop an in-situ forming hydrogel of amorphous nature, which was found to possess many critical elements desirable in a wound dressing such as transparency for wound visualization, good water absorptivity, site conformability, antioxidant activity, optimal water vapour transmission rate and biodegradability.

Hydrogel refers to a three-dimensional polymeric structure, which is water-insoluble but capable of absorbing and retaining large quantities of water to form a stable, often soft and pliable.

The present disclosure relates to a hydrogel comprising at least 4% (w/v) of an enzymatically cross-linked silk sericin, preferably comprising at least 6% (w/v) of silk sericin, more preferably comprising at least 7.5% (w/v) of silk sericin, even more preferably comprising at least 7.8% (w/v) of silk sericin.

In an embodiment, the hydrogel comprises 4-20% (w/v) of an enzymatically cross-linked silk sericin, preferably 6-7.5% (w/v) of an enzymatically cross-linked silk sericin.

In an embodiment, the silk sericin may be enzymatically cross-linked by an enzyme complex selected from the following list: horseradish peroxidase and hydrogen peroxide, laccase, transglutaminase, or mixtures thereof.

In an embodiment, for even better results, the silk sericin may be enzymatically cross-linked with horseradish peroxidase and hydrogen peroxide.

In an embodiment, the silk sericin may be enzymatically cross-linked by horseradish peroxidase and hydrogen peroxide for 10 seconds-5 minutes, preferably for 15 seconds-3 minutes.

In an embodiment, the silk sericin may be enzymatically cross-linked with 0.1-0.6% (w/v) of horseradish peroxidase and 0.15-0.4% (v/v) of hydrogen peroxide.

In an embodiment, the silk sericin may have a molecular weight of is 150-400 kDa, preferably 200-300 kDa.

In an embodiment, a cross-section of the hydrogel now disclosed may have pores with a diameter between 20-100 μm, preferably 20-100 μm, more preferably 50 μm.

In an embodiment, the hydrogel may have a perforation maximum force of 194.0±12.6 N force higher than 150 N, preferably higher than 190 N, more preferably higher than 200 N.

In an embodiment, the hydrogel may have an antioxidant activity of 0.03-0.05 eq [Asc. Ac.]g/L)/g, preferably, more preferably 0.05 eq [Asc. Ac.]g/L)/g.

The present disclosure also relates to a hydrogel for use in medicine, in veterinary, cosmetic or as an in vitro model for cell culture studies.

The present disclosure also relates to a hydrogel for use in the treatment of wound healing, chronic wound healing, acute healing, tissue defect and/or tissue regeneration.

In an embodiment, the hydrogel may be for use in the treatment of chronic wound healing, tissue defect and/or tissue regeneration is selected from the following list: skin wound, skin defect, diabetic wound healing, diabetic ulcer, bone wound, bone defect; joint wound, joint defect; meniscus wound, meniscus defect, articular cartilage, wound, articular cartilage defect, soft tissue wound, soft tissue defect, lung tissue wound, lung tissue defect, kidney wound or kidney defect.

In an embodiment, the hydrogel now disclosed may be for the use in the treatment of cardiovascular wounds or cardiovascular defects, or ischemic, or vascular diseases.

In an embodiment, the hydrogel may further comprise a biological active agent, a therapeutic agent, an additive, a pharmaceutically acceptable excipient, a pharmaceutically acceptable carrier, and mixtures thereof.

In an embodiment, the additive may be a surfactant selected from the following list: polysorbates, cationic molecules or polymers, and mixtures thereof, in particular, the additive may be polysorbate 20, polysorbate 80 or polylysine.

In an embodiment, the biological active agent or the therapeutic agent may be selected from the following list: a natural polymer, a synthetic polymer, a glycoside, a polysaccharide, a terpene, a protein, a peptide, an anti-body, an anti-gene, an antioxidant, an anti-inflammatory, a prebiotic, a probiotic, a nanoparticle, a micro particle, an ion, a mineral, an antibiotic, a coagulation agent, a cell, a stem cell, a ligand, a growth factor, a platelet, and mixtures thereof.

In an embodiment, the antibiotic may be vancomycin, streptomycin, ciprofloxacin, and mixtures thereof.

In an embodiment, the coagulation agent may be thrombin or calcium.

In an embodiment, the hydrogel now disclosed may be transparent.

In an embodiment, the hydrogel is an injectable hydrogel or a topical hydrogel.

This disclosure also relates to an adhesive or a patch comprising the hydrogel now disclosed. The present disclosure also relates to a method for producing the hydrogel herein disclosed and wherein said method comprises the following steps:
- extracting silk sericin by immersing cocoons in water, at 100° C. for 40-60 min, in a ratio of 1-3% weight cocoons/volume of water,
- filtering the silk sericin;
- concentrating the silk sericin to at least 4% (w/v), to at least 6% (w/v), preferably to at least 7.5% (w/v), even more preferably to at least 7.8 (w/v);
- preparing the hydrogel by adding 0.2% (w/v) of horseradish peroxidase, 0.3% (v/v) hydrogen peroxide and at least 4% (w/v) of silk sericin, at least 6%, (w/v), preferably at least 7.5% (w/v), even more preferably at least 7.8% (w/v) of silk sericin to water.
- mixing for at least 10 seconds to 5 minutes, preferably 10 seconds to 3 minutes.

In an embodiment, the extracting step of the silk sericin may also be carried out by boiling or by any other technique using heat. The extracting step of the silk sericin may also be carried out using urea, using acidic conditions, using alkaline conditions, or using a combination of the above-mentioned techniques/conditions.

In an embodiment, the concentrating step may be carried out until a concentration of silk sericin of at least 7.8% (w/v) is reached.

In an embodiment, for even better results, the concentrating step may be carried out until a concentration of silk sericin of 10-90% (w/v) is obtained, preferably 20-60% (w/v), even more preferably 25-40% (w/v).

In an embodiment, the concentrating step may be carried out by evaporation, dialysis, reverse osmosis and using a rotavapor, among others.

In an embodiment, the method for producing the hydrogel now disclosed further comprises steps of adding a biological active agent, a therapeutic agent, an additive, a pharmaceutically acceptable excipient, a pharmaceutically acceptable carrier, and mixtures thereof, before or after the step of preparing the hydrogel, such that the sericin-based hydrogel may comprise said biological active agent, therapeutic agent, additive, pharmaceutically acceptable excipient, pharmaceutically acceptable carrier, and mixtures thereof.

In an embodiment, the silk sericin may also be commercially obtainable.

BRIEF DESCRIPTION OF THE DRAWINGS

The following figures provide preferred embodiments for illustrating the description and should not be seen as limiting the scope of disclosure.

FIGS. 2C and 2D at 1000×.

FIGS. 3A-3C. Structural analysis and optical absorbance profile of the sercin hydrogels. FIG. 3A: Macroscopic image of the formed hydrogels; FIG. 3B: colorimetry evaluation; FIG. 3C: ATR-FTIR spectra of the Hydrogen peroxide, HRP, aqueous sericin solution, the mixture of sericin/HRP/$H_2O_2$ before gelation, and the final formed SHG.

DETAILED DESCRIPTION

In an embodiment, *Bombyx mori* cocoons were supplied by the Portuguese Association of Parents and Friends of Mentally Disabled Citizens (APPACDM, Castelo Branco, Portugal). The other materials and reagents were purchased from Sigma-Aldrich (St Louis, Mo., USA) unless mentioned otherwise.

Figure 1:
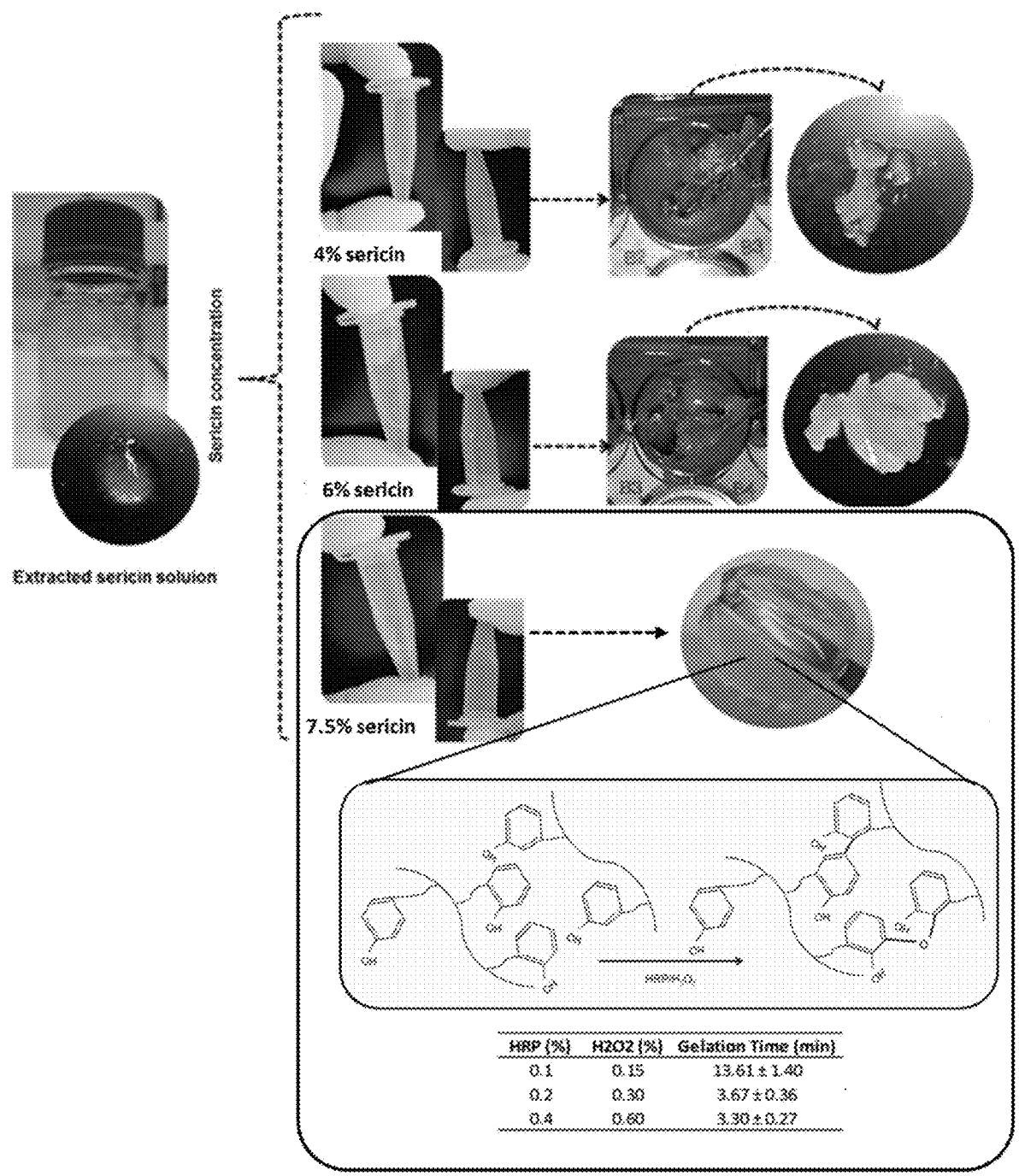
FIG. 1. Schematic illustration of sericin enzymatically crosslinked silk sericin-based hydrogel development and optimization.
Figure 2A:
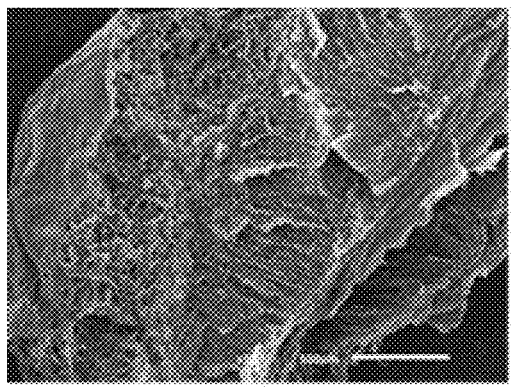
FIGS. 2A-2D. SEM micrographs of lyophilized sericin-based hydrogels at different resolutions FIGS. 2A and 2B at 500×.
Figure 2B:
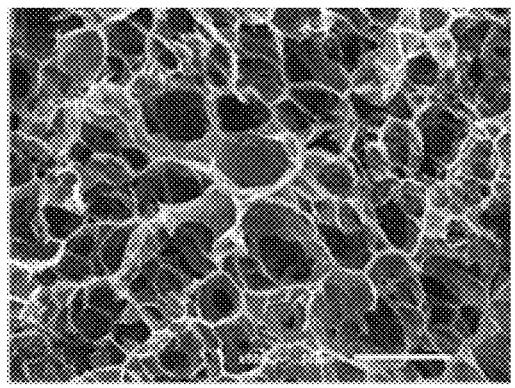
Figure 2C:
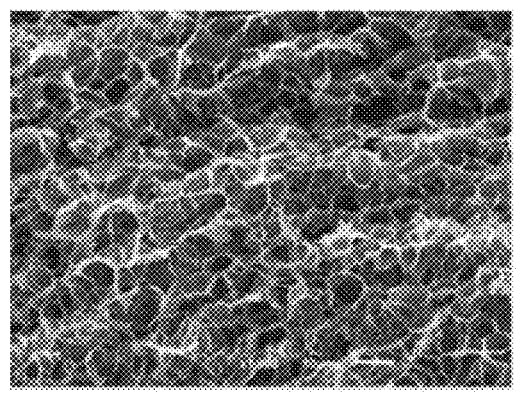
Figure 2D:
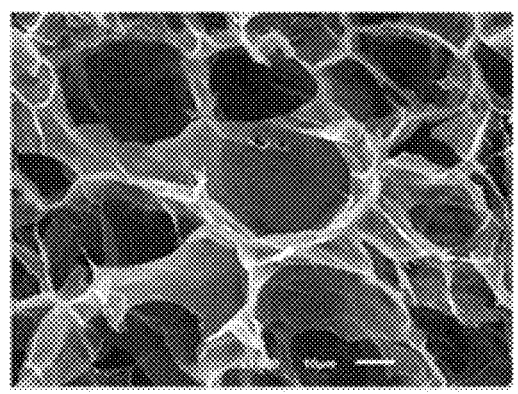

In an embodiment, the preparation of silk solution and sericin-based hydrogels was conducted by sericin extraction by boiling, filtration and concentration to different weight ratios (i.e. 4, 7.5 and 7.8% (m/v)). Solutions were filtered and optimized at a final concentration of 7.5%. The hydrogel was prepared by adding different volumes and concentrations of HRP and hydrogen peroxide until gelation occurred (FIG. 1). The final formulation was fixed using 0.2% (m/v)

HRP, 0.3% (v/v) hydrogen peroxide and 7.5% m/v of sericin, and then mixed for 15 seconds.

In an embodiment, the sericin quantification by dry weight was performed as follows: dry weights were determined by placing sample aliquots of sericin solution and hydrogel at 105° C. to a constant weight. In the end, the total solids were calculated according the equation:

$$\text{Dry weight}(\%) = \frac{(Wd - Wc)}{(Ww - Wc)} \times 100$$

In equation, Wd refers to the dry weight of sample with container; Ww means wet weight of sample with container and Wc refers to the weight of container.

In an embodiment, the sericin quantification by dry weight was determined and values of 0.67±0.05 and 7.54±0.50(%) were obtained for both, extracted sericin solution and final hydrogel formulation, respectively.

In an embodiment, the microstructure evaluation and porosity analysis of the sericin-based hydrogel were performed by scanning electron microscopy (SEM). For this purpose, hydrogels were cast in moulds and immersed in liquid nitrogen to avoid the development of ice crystals, before freeze-drying. SEM was operated at low vacuum mode, using a spot size of 27-28 and a potential of 30 kV. All analyses were performed at room temperature, in particular at 20° C.

In an embodiment, the morphology and microstructure of the sericin-based hydrogel were examined by SEM at different resolutions (FIGS. 2A-2D). Prior to the analyses, the specimens were immersed in nitrogen to avoid the formation of ice crystals and then lyophilized. Among the cross-section of the sericin hydrogels were observed pores, showing the potential permeability of the hydrogels. From the obtained images, pores were noted with approximately 50 μm.

In an embodiment, the structure and chemical analysis of sericin-based hydrogel were performed: sericin solution, HRP, hydrogen peroxide solution and the formed sericin-based hydrogels were further analysed by Infrared spectroscopy analysis in a Spectrum Series, Perkin Elmer FTIR spectrometer (ABB, Switzerland) equipped with attenuated total reflectance (ATR) sampling accessory (PIKE Technologies, USA), and a diamond/ZnSe crystal. All spectra were acquired using 16 scans and a 4 $cm^{-1}$ resolution in the region of 4000-700 $cm^{-1}$. In addition, baseline—point adjustment and spectra normalization was performed. PBS solution was used as background in the FTIR. All samples used were and run in triplicate, and the data presented were the average of the three measurements.

In an embodiment, sericin-based hydrogel was successfully developed via HRP mediated cross-linking in physiological condition and presented transparent appearance, as showed in FIG. 3A. The hydrogel color was evaluated (FIG. 3B) using a portable Chroma meter CR-400 (from Minolta Chroma, Osaka, Japan). A CIELab color scale was employed to measure the degree of lightness (L), redness (+a) or greenness (−a), and yellowness (+b) or blueness (−b) of the films, under D65 (daylight). Hydrogel specimens were measured on the surface of the white standard plate, with color coordinates Lstandard=97.6, astandard=0.01 and bstandard=1.60. The color of the hydrogel was expressed as the total difference in color (DE), three samples were taken e and, on each hydrogel piece, four readings were made on each side, as previously described. Apparently as it can be seen in (FIG. 3A) sericin-based hydrogel were transparent, flexible and homogeneous. Their surfaces appeared smooth, without visible pores or cracks.

The ATR-FTIR spectra (FIG. 3C) demonstrated that one of the absorbance peaks of the hydrogels was at 1549 $cm^{-1}$, at the same position with the ones from the sericin solution and the mixed solution of sericin/HRP/$H_2O_2$, which were located also at 1549 $cm^{-1}$. Additionally, all these three spectra presented also absorbance peaks at 3383 $cm^{-1}$. The results are in accordance with previous similar works based on different sericin hydrogel or considering other silk based-hydrogels.

In an embodiment, the differential scanning calorimetry analysis of the sericin-based hydrogel was conducted: thermograms were obtained using a DSC (DSC-60, Shimadzu, Columbia, USA). Hydrogels were prepared and kept at refrigerated conditions (4° C.) for 24 h, than 5.0 mg of the hydrogel were crimped in a standard aluminium pan and heated from 20° C. to 350° C. at a heating constant rate of 10° C./min under constant purging of nitrogen at 20 mL/min. All samples were run in triplicate and data presented were the average of the three measurements.

Figure 4:
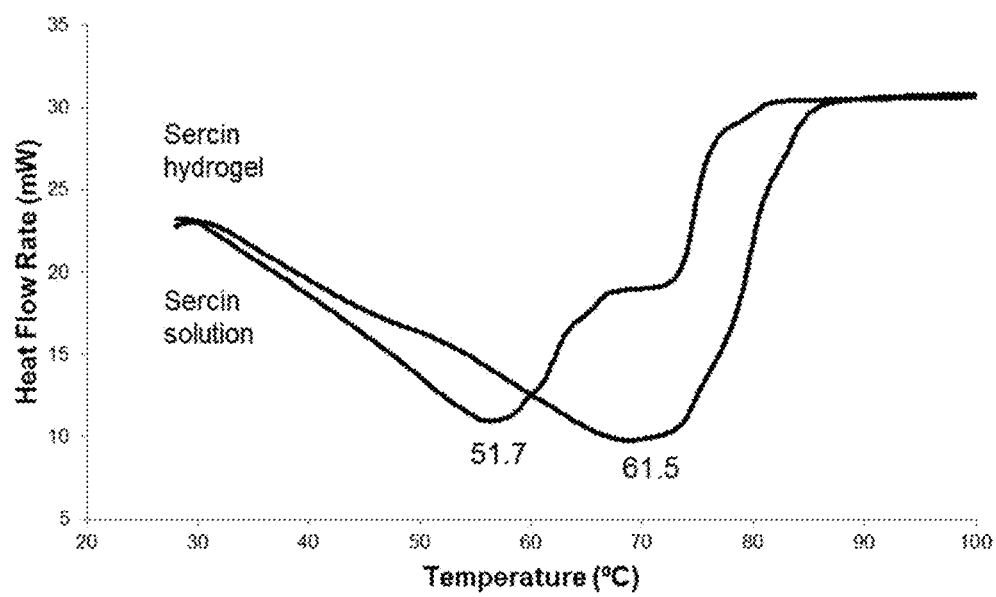
FIG. 4. Thermogram of sercin solution and sericin-based hydrogel.
Figure 5A:
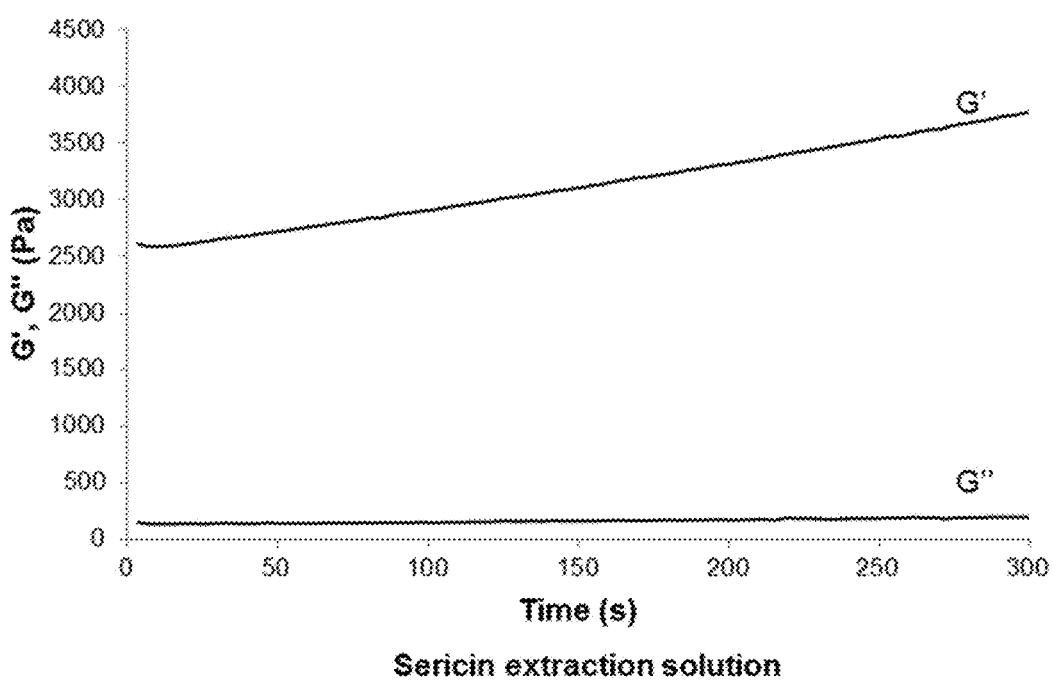
FIGS. 5A-5B. Oscillatory scans displaying both the elastic modulus (G') and viscous modulus (G") of sercin extraction solution (FIG. 5A), and enzymatically crosslinking hydrogel (FIG. 5B).
Figure 5B:
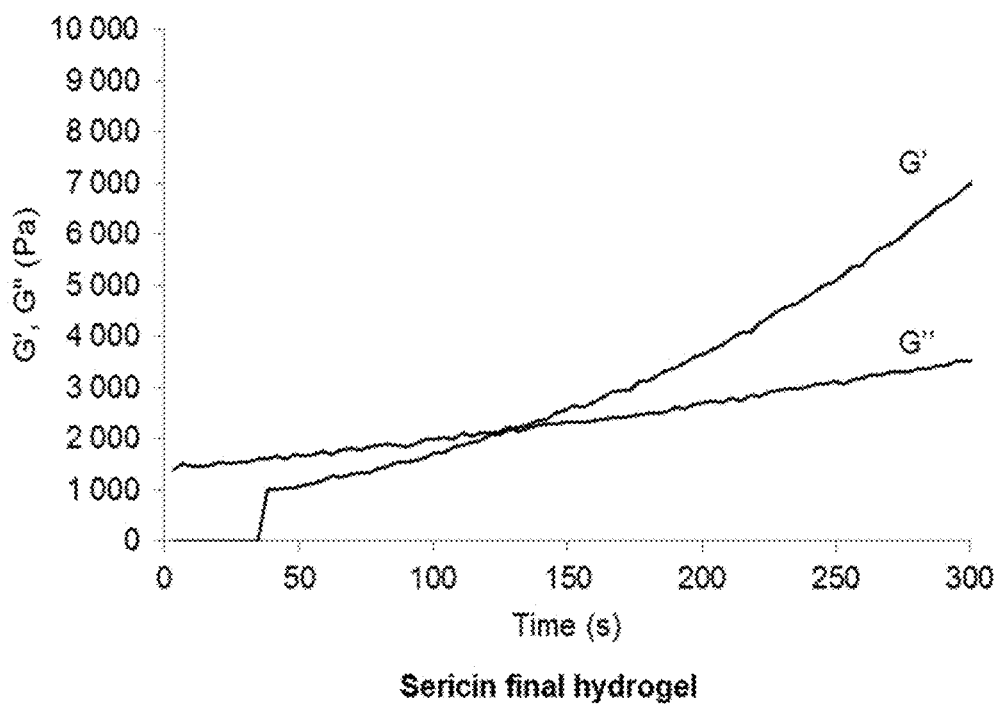

In an embodiment, the similar thermal behavior was observed in both thermograms of sericin-based hydrogel and sericin solution (FIG. 4), respectively. In the sericin solution curve, an endothermic peak of 51.7° C. was observed, while in the sericin-based hydrogel an endothermic peak of 61.5° C. was shown. In the sericin solution one peak at low temperature (round 75° C.), may be due to the evaporation of water. In the same curve it was not observed at high temperatures (below 200° C.) any peak like it has been described in literature (endo peak at 212° C.), attributed to thermal decomposition of sericin with oriented n-sheet configuration. This confirms the amorphous status of sericin in the extraction solution. The thermal difference (of 10° C.) in sericin solution and sericin based hydrogel may be due to the enzymatically crosslinking effect, that turns this final formulation more thermal stable.

In an embodiment, mechanical tests of the sericin-based hydrogel was performed. The compression and perforation properties of hydrogels, were measured according to the Texture Analyser TXT plus from Stable Micro Systems (UK). The Exponent software was used for Ottawa cell with 6.5 mm holes, and 2 mm Dia cylinder stainless method. The hydrogels samples were prepared in a 24 wells plate (diameter of 1.5 cm and thickness of 3 mm). At least three disks of each hydrogel sample were analysed.

Regarding the compression and perforation mechanical tests, sericin-based hydrogel were compared with well-described agar hydrogels at 1%. For the same distance (1.286 mm), and for 6 replicates of each formulation.

This result clearly opens a new lack of opportunities for this novel hydrogel considering applications such as wound dressings, or other medical applications that requires resistant hydrogels, with good mechanical proprieties.

In an embodiment, the rheology assessment of the sericin-based hydrogel was conducted. Oscillatory shear rheological tests were performed using a controlled stress rheometer (CS-50, Bohlin Instruments, Cranbury N.J., USA), with a cone-and-plate geometry (diameter 40 mm and angle 2°) fitted at 115 μm gap. The temperature of the bottom plate was controlled with a Peltier system. Immediately after preparation approximately 1.5 mL of the solution was transferred to the rheometer equilibrated at 25° C. Testing was then performed at low strain amplitude (1%) and low frequency (1 Hz), within the linear viscoelastic range—as assessed by stress and frequency sweep experiments, respectively. The gel development was assessed by measuring the storage modulus (G') and the loss modulus (G") through time sweep experiments (25° C., 1 Hz and 1%) carried out for approximately 1 h.

In an embodiment, in vitro swelling ratio and degradation profile of the sericin-based hydrogel was performed. The prepared sericin-based hydrogel discs in 96 wells microplate, with 100 μL in each well, were used for the swelling and degradation study. The swelling ratios of the hydrogels were tested in both ultrapure water and PBS at 37° C. Each piece of hydrogel was placed in an eppendorf with 1 mL PBS or ultrapure water (0.55 μS/cm) prepared by a ultrapure water system (Millipore Q, Advantage A10, Germany), subsequently the samples were placed in a thermostatic water bath (Dubinoff bath BSD/D, Cambridgeshire, UK) at 37° C. The wet weight of the sample was measured at 1, 2, 4, 6, and 24 hours. Before weighting, surface liquid in the hydrogels were absorbed by tissue. The swelling ratio at each time point was calculated as following equation 1:

$$\text{Swelling ratio}(\%) = \frac{wt - wd}{wd} \times 100$$

In Equation 1, wt referred to the wet weight of the sample tested in different time point, and wd is the dry weight of the sample. It was assumed that the dry weight of each specimen was constant during the tested time-period.

Figure 6:
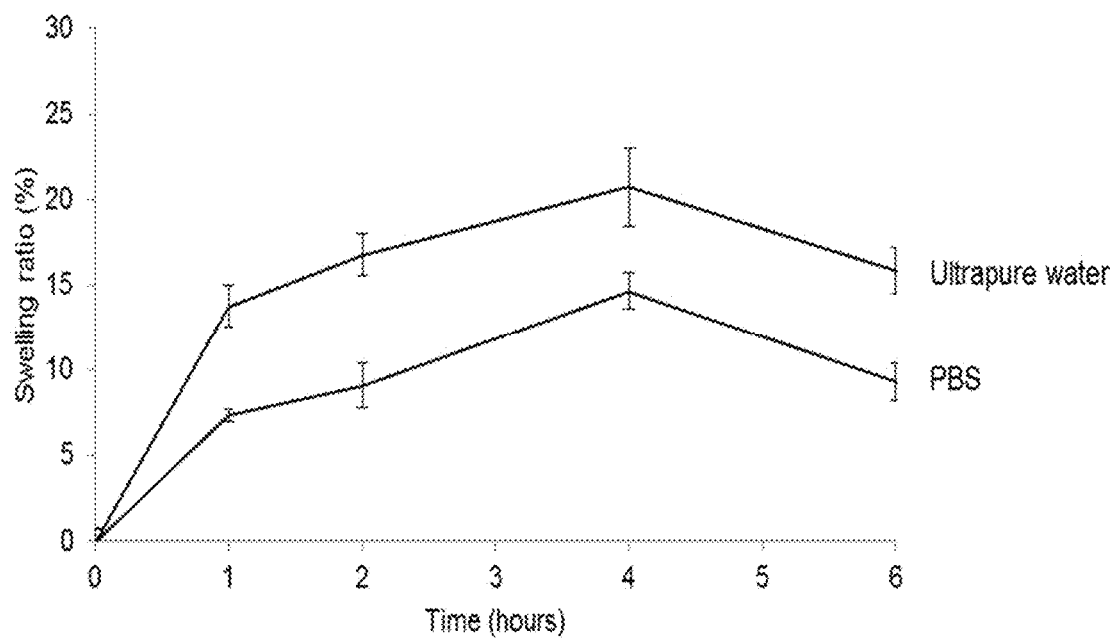
FIG. 6. Swelling ratio profiles of the sericin-based hydrogel in PBS and Ultrapure water at 37° C.

FIG. 6 showed the swelling behavior of the sericin hydrogel in PBS and ultrapure water. The sericin hydrogel reached the maximum swelling profile after 4 hours immersion in ultrapure water higher than in PBS. Sericin hydrogel presented a high swelling ratio of 21% in water and 15% when immersed in PBS. Higher swelling profiles are documented in other silk-based hydrogels. Nonetheless, the sericin hydrogel are more stable in water and PBS, regarding physiological conditions for long periods of time than other silk-based hydrogels, as it can be described in enzymatic degradation profile (FIG. 7B).

In an embodiment, for degradation assay hydrogels were tested in both PBS and PBS with Protease XIV from *Streptomyces griseus* at physiological concentration of 3.2 U/mg, according to previous works (30). Each piece of hydrogel was placed in an Eppendorf with 1 mL of each solution and then samples were placed in a thermostatic water bath (Dubinoff bath BSD/D, Cambridgeshire, UK) at 37° C. The wet weight of the sample was measured at 1, 2, 4, 6, 24, 48, 72, 96, 168, 240 and 312 hours. The degradation ratio at each time point was calculated as following equation 2:

$$\text{Weight loss}(\%) = \frac{wi - wt}{wi} \times 100$$

In equation 2, wi means the initial wet weight of the hydrogel, and wt is the wet weight tested at each point.

In an embodiment, the pH responsiveness of the sericin-based hydrogels was performed. Sericin-based hydrogel discs in 96 wells microplate, with 100 μL in each well were immersed in 0.154 M NaCl solution (pH 7.4) (Panreac) at 37° C. overnight. The wet weights of the hydrogels were measured and then the hydrogels were immersed in 1 mL of NaCl solutions at different pH values (37° C.): 2.5, 5.5, 6.5 and 8.5. These pH values were selected according the pH values of healthy skin or injured skin. Healthy skin or acute wounds exhibit slightly acidic pH (pH values of 5.5-6.5) and chronic wounds have pH values higher than 7.4 caused by the microbial proliferation. Occasionally, the irregular vascularization of chronic wound is responsible for a heterogeneous dissemination of infection in the wound bed, causing drastic pH variations (31). The pH values were adjusted by addition of NaOH 1M (Merck, Darmstad, Germany) or HCl 1M (Merck, Darmstad, Germany). As control, the hydrogels were also immersed in methanol to undergo n-sheet conversion. After 2 h, 24 h, 96 h the wet weights of the hydrogels were recorded again after removing surface liquid. The wet weight variation was calculated as equation 3.

$$\text{Wet weight variation}(\%) = \frac{wt - wi}{wi} \times 100$$

In equation 3, wi means initial weight of the hydrogel after overnight immersion in 0.154 M sodium chloride solution, and wt refers to the wet weight tested during alternating immersion. The prepared discs were also immersed in methanol for 3 h to undergo 0 sheet conversion and then the opaque hydrogels were used as control for the response test as well as for swelling ratio and degradation tests.

Figure 7A:
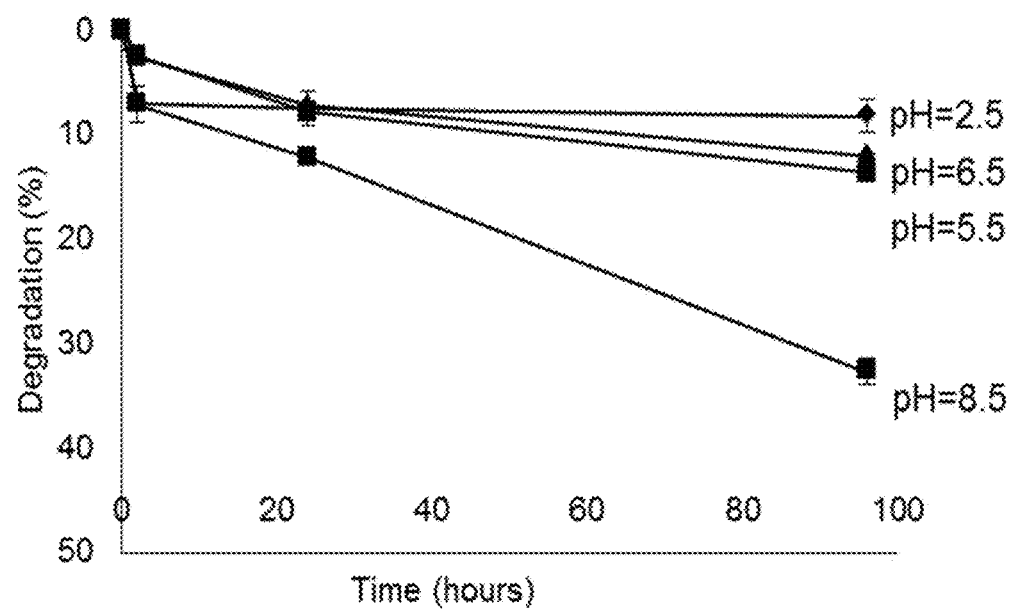
FIGS. 7A-7B. Degradation response of sericin-based hydrogels: pH degradation during 96 hours (FIG. 7A) and enzymatic degradation with protease XVI during 400 hours (FIG. 7B), both at 37° C.
Figure 7B:
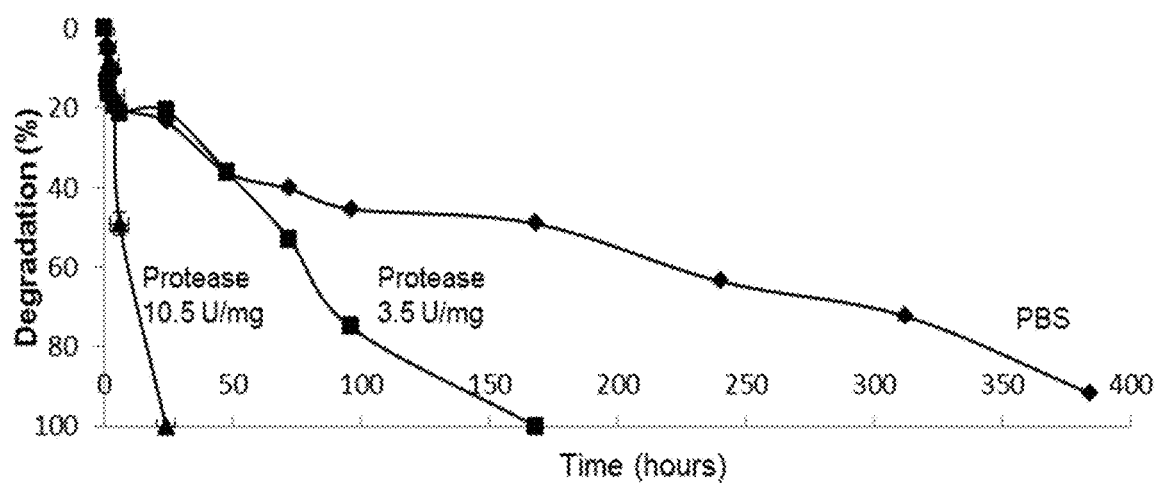

The hydrogels were submitted at different pH values similar to acute and chronic wounds (FIG. 7A). At pH values between 2.5 and 6.5, it was observed a slight gel shrinking during the time tested, at pH value of 8.5 was detected an higher reduction (nearly 30%). However, in all cases only a reduction between 7-12% was observed after 24 h. These results demonstrated that the hydrogel is pH resistant comparing to other studies made with other silk hydrogels. Our pH responsiveness assay was performed for 4 days, being superior to previous studies. Therefore, sericin gel demonstrated to be a promising biomaterial for acute as well as for chronic wounds.

The FIG. 7B shows the enzymatic degradation profiles of sericin-based hydrogel. It was observed that these hydrogels degraded over 72 h in physiological protease concentration (3.5 U/mg) degraded only 40% at 37° C. Moreover and in PBS at 37° C. the formulations were stable for 16 days with a degradation of 91% (w/w). These results were higher than similar silk fibroin hydrogels also mediated by HRP/$H_2O_2$, in which the complete degradation was over 6 h, considering a smaller concentration of protease (e.g. 0.0005 U/mL).

The FIG. 7B also shows the enzymatic degradation profile of sericin-based hydrogel, simulating acute and chronic wounds with a protease concentration 3× times higher (10.5 U/mg) than the physiological described in literature (of 3.5 U/mg). It was observed that these hydrogels degraded completely only in 6 hours even in this acute enzyme concentration. This results stills notable regarding other crosslinked silk hydrogels.

Figure 8A:
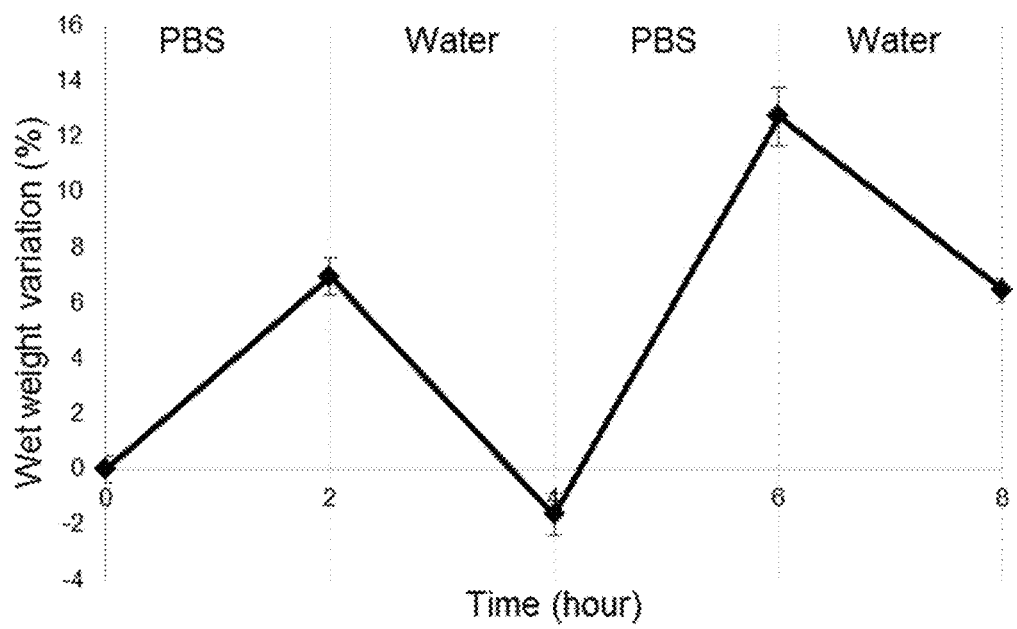
FIGS. 8A-8B. Ionic strength stimuli response of sericin-based hydrogels. The prepared hydrogel discs were alternatively immersed in: PBS and distilled water and each immersion lasted for 2 h (FIG. 8A) and 0.154M and 2M of sodium chloride solutions (FIG. 8B) (both of pH 7.4).
Figure 8B:
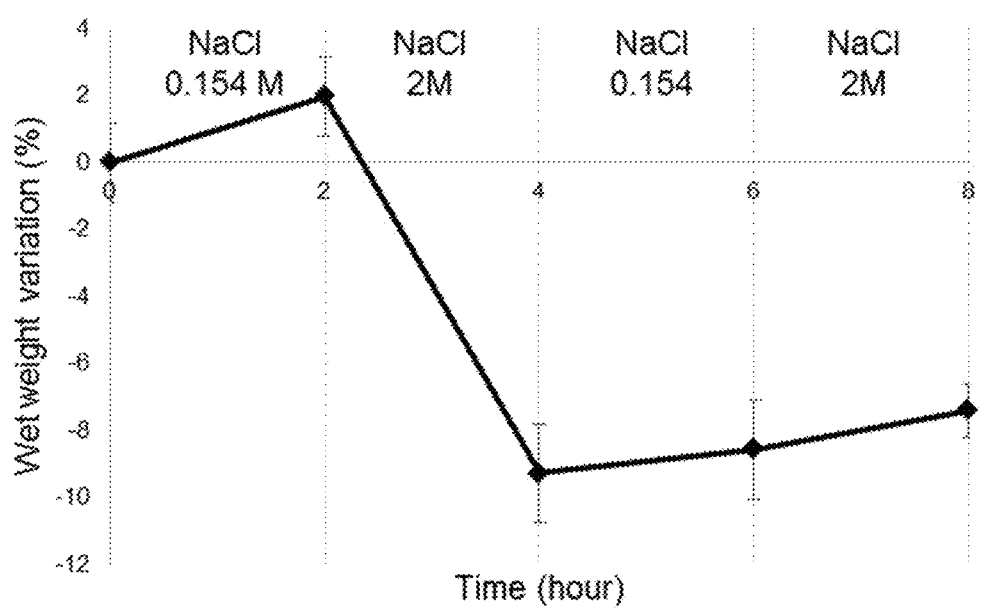
Figure 9:
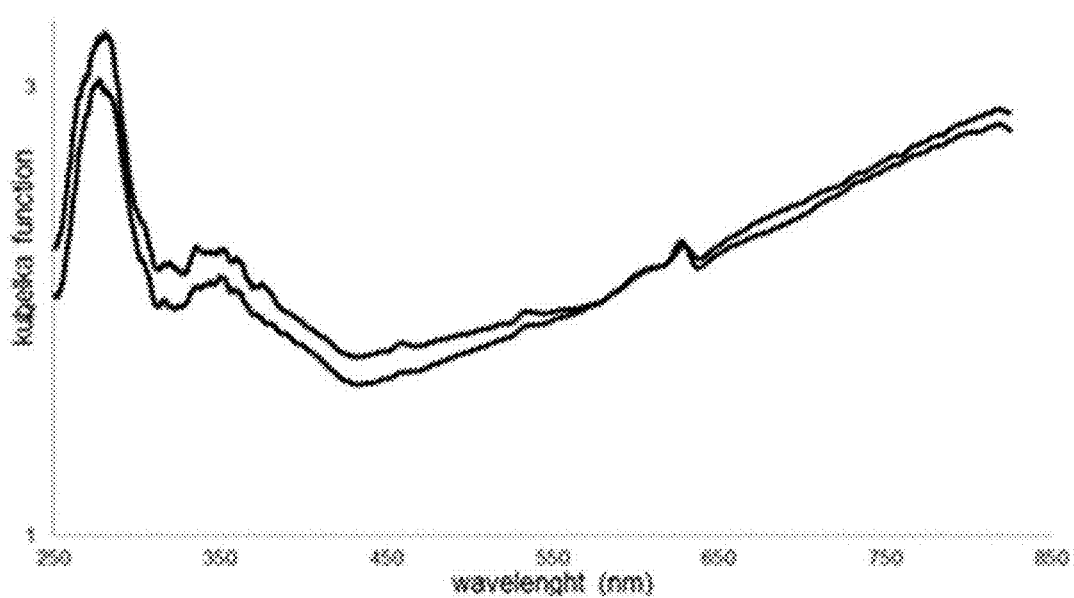
FIG. 9. UV-Vis absorbance spectra of the materials. Kubelka-Munk function plot analysis used in the determination of band.
Figure 10A:
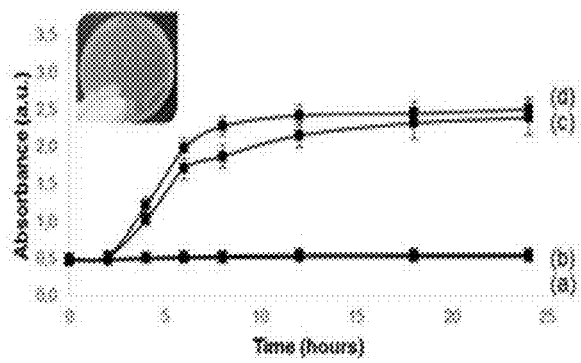
FIGS. 10A-10D. Antimicrobial activity against *Staphylococcus aureus* ATCC 29213 (FIG. 10A), *Staphylococcus aureus* DSM 11729 (FIG. 10B), *Pseudomonas aeruginosa* (FIG. 10C) and *Escherichia coli* ATCC 25922 (FIG. 10D) for sericin solution and Macroscopic image of the well diffusion assay for each microorganism in 6 replicate hydrogels (Scale bar: 9 cm). For each figure (FIGS. 10A-10D), letters represent: (a) negative control, sericin without inoculum, (b) negative control, Muller-Hinton Broth without inoculum, (c) positive control, Muller-Hinton Broth with inoculum and (d) Sericin solution (0.67%) with inoculum.
Figure 10B:
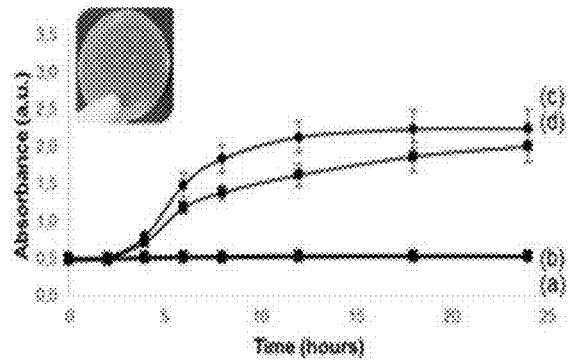
Figure 10C:
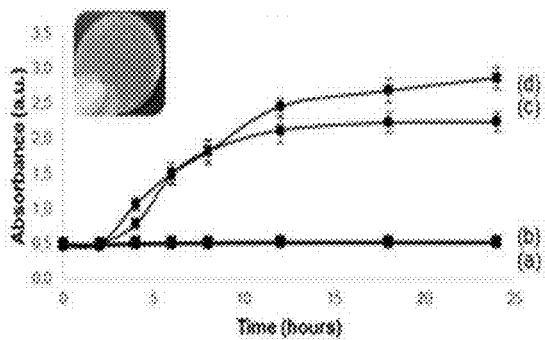
Figure 10D:
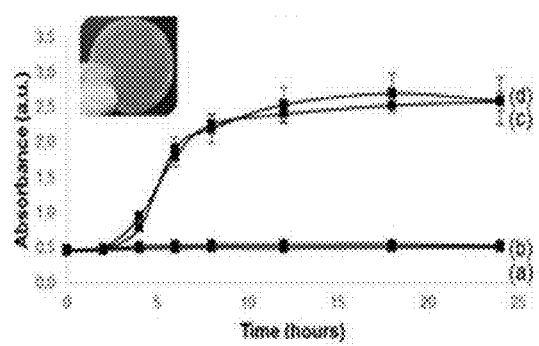
Figure 11A:
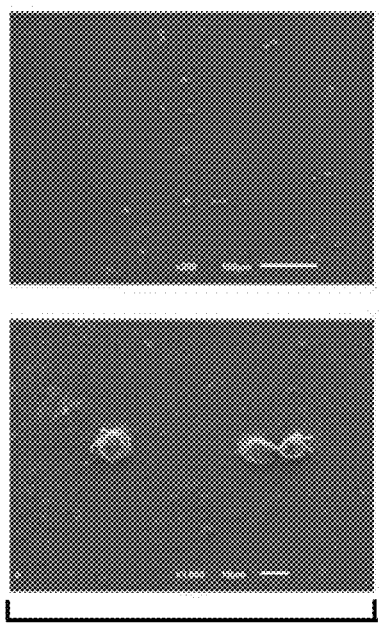
FIGS. 11A-11C. SEM micrographs of fibroblasts seeding in sericin-based hydrogels at different resolutions at 24 (FIG. 11A), at 48 h (FIG. 11B), at 72 h (FIG. 11C), top micrograph in each figure in 200× resolution and bottom micrographic in each figure in 1000×.
Figure 11B:
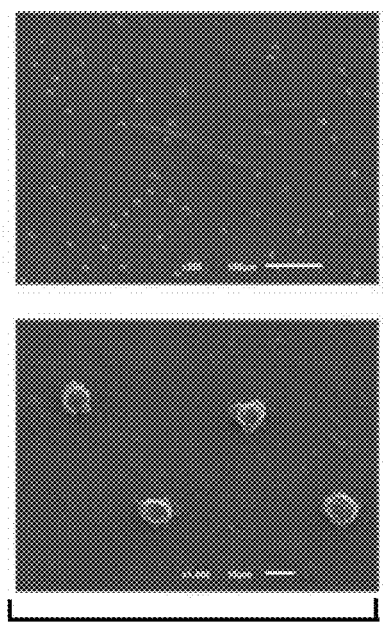
Figure 11C:
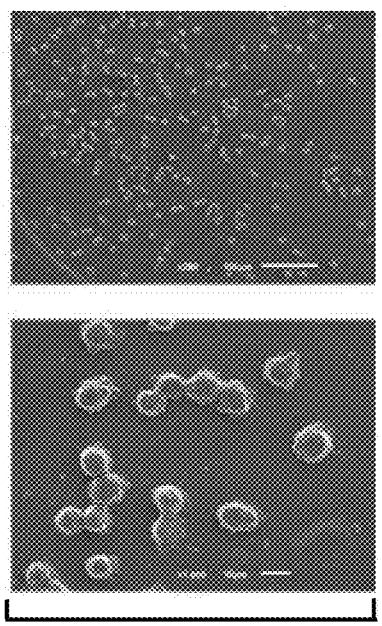
Figure 12:
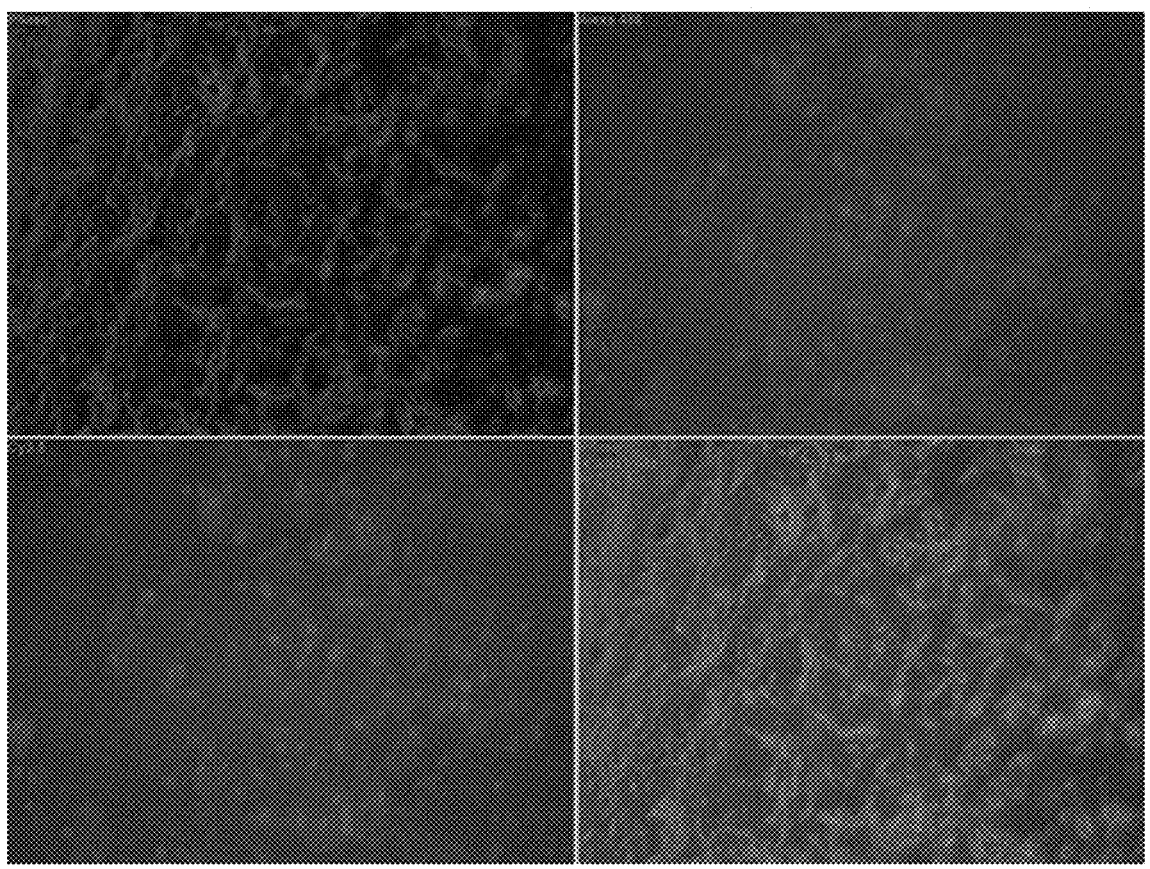
FIG. 12. Micrographs of Live/Dead test, of fibroblasts seeding in sericin-based hydrogels at different resolutions after 72 h f seeding at 200× resolution and down figures in 1000×.
Figure 13:
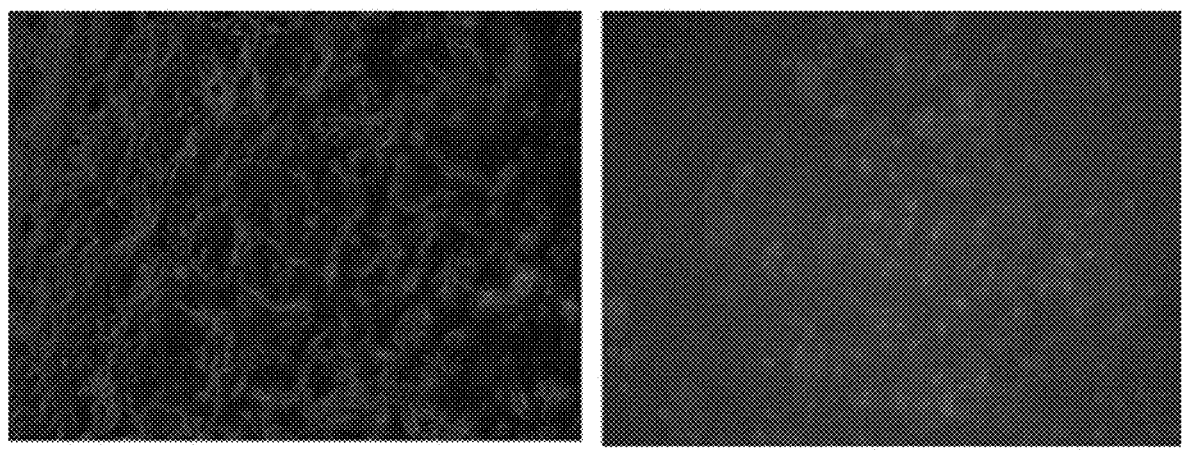
FIG. 13. Micrographs of Live/Dead test, of fibroblasts seeding in sericin-based hydrogels at different resolutions after 72 h f seeding at 200× resolution and down figures in 1000×.
Figure 14:
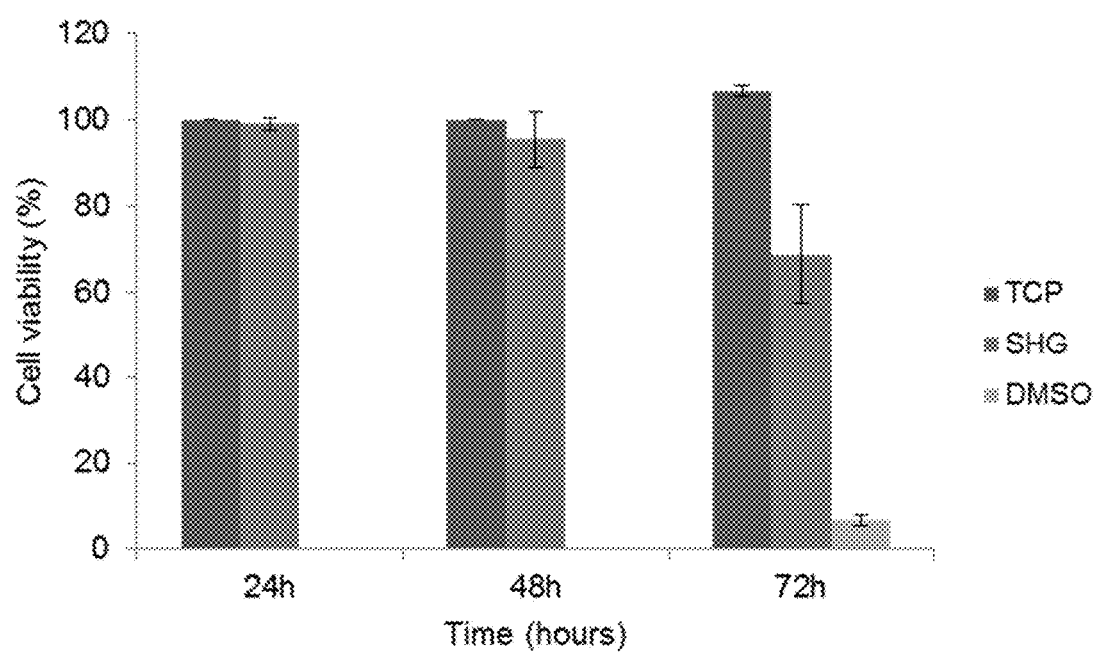
FIG. 14. Effect of SHG on viability of L929 cell lines after 24 h, 48 h and 72 h. Tissue culture polystyrene (TCP) and DMSO were used as positive and negative controls respectively. The results were the mean of 4 replicates, bars represent standard deviation.

The results of the ionic strength responsive are presented in FIGS. 8A-8B. According these data, the weight of sericin-based hydrogels varied with the osmotic pressures of these specimens in water and PBS. In water, it was observed a weight increase, which is in accordance to the swelling ratios. The variations in the weight were reversible in this system. In order to also test the influence of different ions, hydrogels were alternately immersed in a solution of 0.154 M and 2.0 M NaCl. The weight of hydrogel diminished around 9% when the specimens were changed of a solution of 2M to a 0.154 M. Moreover, after this weight variation, the hydrogel remained stable even with the molarities alterations, which showed that the system was not reversible in this ionic strength disparity.

In an embodiment, the ionic strength responsiveness of the sericin-based hydrogel was performed. Sericin-based hydrogel discs in 96 wells microplate, with 100 μL in each well were used for the ionic strength response assay. Firstly, the hydrogels were immersed in 1 mL of PBS at 37° C. overnight and the wet weight of each hydrogel was measured. After this procedure, hydrogels were alternately placed in deionized water and PBS every 2 h during 8 h and the wet weights of the hydrogels were recorded. For the second part of the test, the hydrogels were immersed at 37° C. overnight in 1 mL 0.154M sodium chloride solution (pH 7.4, adjusted by 1.0 M NaOH) and the wet weight of each hydrogel was noted. Then, hydrogels were alternately immersed in 1 mL 2 M sodium chloride (pH 7.4) and 0.154 M sodium chloride solution (pH 7.4) every 2 h during 8 h. Before every change of solution, the wet weights of the hydrogels were measured. All the samples were maintained in the thermostatic water bath at 37° C. The wet weight variation ratio was calculated according to previous equation 3.

In an embodiment, the UV assays were performed using UV-vis spectra were taken using a Shimadzu UV 3100 spectrometer equipped with an integrating sphere, covering a wavelength range between 250 and 850 nm (0.2 nm step-size, $BaSO_4$ as the reference).

In an embodiment, in order to investigate hydrophilic/hydrophobic nature of hydrogels, the water contact angle (WCA) was measured using an Optical Contact Angle (Dataphysics, Germany). WCA was performed using a sessile drop with a volume of 3 μL and measured with the OCA 20 software according Young-Laplace model.

In an embodiment, sericin being more hydrophilic than silk fibroin (due to higher content of polar amino acids including serine, aspartic acid and glutamic acid), silk films become more hydrophilic with increasing sericin content, which results in lower contact angles (i.e. 33.23±4.48 degrees).

In an embodiment, the antioxidant activity was determined, in particular the free radical-scavenging activity was determined by 2,2-azinobis-3-ethylbenzo thiazoline-6-sulphonic acid (ABTS) radical decolourization assay. The radical cation was produced by reacting ABTS with potassium persulfate. The antioxidant potential was measured according to the percentage of inhibition (PI), to be between 20% and 80%, to guarantee a linear response of the analytical method, after 6 min of reaction with 1 mL of diluted ABTS+ solution. Calibration curve was prepared with ascorbic acid in the range of 0.018-0.125 mg/mL and all the determinations accomplished in triplicate. In this assay, sericin solution after extraction and sericin-based hydrogel under physiological protease (3.5 U/mg) degradation after 24 h at 37° C., were used to evaluate the antioxidant potential. The total antioxidant capacity was expressed as mg ascorbic acid equivalent/mL.

In an embodiment, the determination of the antioxidant capacity was performed by ABTS (2,2-azinobis (3-ethyl-benzothiazoline-6-sulphonic) acid) diammonium salt test (SigmaAldrich, St. Louis, Mo., USA). The antioxidant potential was measured according to the percentage of inhibition (PI), to be between 20% and 80%, to guarantee a linear response of the analytical method, after 6 min of reaction with 1 mL of diluted ABTS•+ solution. The total antioxidant capacity was expressed in (eq [Asc. Ac.]g/L)/g extract. For this purpose sericin solution and sericin-based hydrogel were monitored to evaluate the antioxidant potential after sericin extraction, and after 24 h at 37° C. under physiological protease (3.5 U/mg) degradation.

In an embodiment, the results have shown that even considered only a 20% of hydrogel degradation (according to the in vitro degradation profile, mentioned before) the sericin hydrogel showed antioxidant activity values of 0.053±0.002 (eq [Asc. Ac.]g/L)/g extract). In the other hand sericin solution showed antioxidant activity values of 0.032±0.008 (eq [Asc. Ac.]g/L)/g extract). There results clearly highlight the high antioxidant activity potential of sericin and of these novel crosslinked sericin hydrogels.

In an embodiment, $Staphylococcus\ aureus$ DSM 11729, $Staphylococcus\ aureus$ ATCC 29213, $Pseudomonas\ aeruginosa$, and $Escherichia\ coli$ ATCC 25922 were obtained by collection culture of CBQF, Catholic University of Portugal. The isolates were growth aerobically on Nutrient agar (Merck, Darmstad, Germany) at 37° C. for 24 h.

In an embodiment, the antimicrobial activity of sericin solution was determined using an inoculum of 0.5 MacFarland ($1.5 \times 10^8$ CFU/mL) of each bacteria. Muller-Hinton broth (Biokar) 180 μL with sericin solution with 0.67% was inoculated with 20 μL of each bacteria. Three controls were simultaneously assessed, one with 0.67% of sericin solution without inoculum, other with the Muller-Hinton broth with the inoculum and without the inoculum, each in triplicate. The absorbance was measured in a microplate reader (Fluostar Optima, BMG Laptech) at 620 nm during 24 h at 37° C.

In an embodiment, the screening of antimicrobial activity of sericin-based hydrogels was performed by well diffusion assay. Plates of Nutrient Agar were seeded with an inoculum of 0.5 MacFarland ($1.5 \times 10^8$ CFU/mL) of each bacteria. Wells with a diameter of 4 mm were punctured into the plates and filled with 20 μL of hydrogel. Plates were incubated for 24 h at 37° C. The presence or absence of translucent halo zones around the wells were considered as positive or negative for antimicrobial activity, respectively. Control negative was made with Ringer's solution and assays were done in triplicate.

In an embodiment, a mouse fibroblast cell line (L929), acquired from the European Collection of Cell Cultures (ECACC, United Kingdom) and used at passages 30-32. Cells were grown as monolayer cultures in Dulbecco's Modified Eagle's Medium (DMEM; Sigma Aldrich; Germany) supplemented with 10% fetal bovine serum (FBS; Biochrom, Germany) and 1% antibiotic-antimycotic liquid (Gibco, UK). The cells were incubated in a $CO_2$ incubator under an atmosphere of 5% $CO_2$ at 37° C., with medium change every two days. At confluence cells were detached from the culture flasks using TrypLE Express (1×) (Life Technologies, Carlsbad, Calif., USA), centrifuged, resuspended in the cell-culture medium, and seeded in the hydrogel at a density of ($1.0 \times 10^4$ cells/mL). The cell-seeded hydrogel were also incubated at 37° C., 5% $CO_2$ and 95% humidity, for 1, 2, and 3 days. Tissue culture polystyrene (TCPS; Sarstedt) coverslips and SF membranes were used as control surfaces (33).

In an embodiment, sericin-based hydrogel were prepared in aseptic conditions, in a sterile cabinet and used for the cell encapsulation. A warmed mixture (500 μL) was mixed with the cell pellet (cell suspension containing: $1.0 \times 10^4$ cells/mL) and got a homogeneous cell suspension, and every 50 μL of the cell suspension was transferred into one piece of cover slips with 13 mm diameter (Sarstedt, Newton, N.C., USA) in a 24-well suspension cell culture plate. The plate was then placed into the $CO_2$ incubator for around 10 minutes to allow the gelation. After the gel was formed, 1 mL (DMEM) alpha medium was supplemented into each well, and the medium was changed every two days. The Live/Dead of the incorporated cells was evaluated by Calcein AM and propidium iodide (Molecular Probes*; Life Technologies, Carlsbad, Calif., USA) staining, after culturing for 1, 2 and 3 days. For this assay, the hydrogels with cells were washed by PBS, and then immersed in 1 mL PBS supplemented with 1 μg Calcein AM and 2 μg propidium iodide for 30 minutes. The samples were observed in a transmitted and reflected light microscope (Axio Imager Z1m, Zeiss, Jena, Germany) after washing by PBS (34). The effect of hydrogels on cell viability was measured at selected concentrations using the methylthiazolyldiphenyl-tetrazolium bromide conversion (MTT) assay at 1, 2 and 3 days. For this assay, 100 μL MTT (5 mg/mL in PBS) working solution was added into each well, followed by incubated for 2 hours. The absorbance of 50 μL supernatant from each well was read in a microplate reader (Fluostar Optima, BMG Laptech) at 570 and 690 nm. Hydrogels without cells were used as control. Each treatment was tested in four individual wells. The negative control used, was also DMSO. The plates were shaken on an orbital shaker to solubilize the crystals of formazan. The hydrogels encapsulated with cells were frozen and then lyophilized, after culturing for 3 days, respectively. The morphology of the hydrogels was observed by scanning electron microscopy (SEM). (JEOL-5600 Lv microscope, Japan) observation, the samples after coated with a layer of Au/Pd SC502314B in an evaporator coater (E6700, Quorum Technologies, East Grinstead, UK).

In an embodiment, the MTT test demonstrates biocompatibility and capacity for cell encapsulation of the hydrogel disclosed in the present subject matter.

In an embodiment, the hemocompatibility studies demonstrate excellent blood compatibility, exhibiting low hemolysis ratio, anti-coagulant and anti-thrombogenic activities of the hydrogel disclosed in the present subject matter.

Throughout the description and claims the word "comprise" and variations of the word, are not intended to exclude other technical features, additives, components, or steps. Additional objectives, advantages and features of the solution will become apparent to those skilled in the art upon examination of the description or may be learned by practice of the solution.

The term "comprising" whenever used in this document is intended to indicate the presence of stated features, integers, steps, components, but not to preclude the presence or addition of one or more other features, integers, steps, components or groups thereof.

It will be appreciated by those of ordinary skill in the art that unless otherwise indicated herein, the particular sequence of steps described is illustrative only and can be varied without departing from the disclosure. Thus, unless otherwise stated the steps described are so unordered meaning that, when possible, the steps can be performed in any convenient or desirable order.

The disclosure should not be seen in any way restricted to the embodiments described and a person with ordinary skill in the art will foresee many possibilities to modifications thereof.

The above-described embodiments are combinable.

The following claims further set out particular embodiments of the disclosure.

The following references, should be considered herewith incorporated in their entirety:

1. Boateng J, Burgos-Amador R, Okeke O, Pawar H. Composite alginate and gelatin based bio-polymeric wafers containing silver sulfadiazine for wound healing. International Journal of Biological Macromolecules. 2015; 79:63-71.
2. Jin S G, Yousaf A M, Kim K S, Kim D W, Kim D S, Kim J K, et al. Influence of hydrophilic polymers on functional properties and wound healing efficacy of hydrocolloid based wound dressings. International Journal of Pharmaceutics. 2016; 501 (1-2): 160-6.
3. Phillips C J, Humphreys I, Fletcher J, Harding K, Chamberlain G, Macey 4 S. Estimating the costs associated with the management of patients with chronic wounds using linked routine data. International Wound Journal. 2015; ISSN 1742-4801.
4. Hurd T. Understanding the financial benefits of optimising wellbeing in patients living with a wound. Wounds International. 2013; 4(2):13-7.
5. Kathleen M. Understanding and overcoming the challenges of effective case management for patients with chronic wounds. The Case Manager. 2005; 16(2):62-7.
6. Petrie N C, Yao F, Erickson E. Therapy in wound healing. Surgical Clinics of North America. 2003; 83:194-9.
7. Sen C K, Gordillo G M, Roy 5, Kirsner R, Lambert L, Hunt T K, et al. Human skin wounds: a major and snowballing threat to public health and the economy. Wound Repair and Regeneration. 2009; 17:763-71.
8. Sivaranjani V, Philominathan P. Synthesize of Titanium dioxide nanoparticles using Moringa oleifera leaves and evaluation of wound healing activity. Wound Medicine. 2016; 12:1-5.
9. Frykberg R G, Armstrong D G, Giurini J, Edwards A, Kravette M, Kravitz 5, et al. Diabetic foot disorders: a clinical practice guideline. Journal of Foot and Ankle Surgery. 2000; 39 (5 Suppl): S1-60.
10. Macdonald J M, Geyer M J. Wound and lymphoedema management. World Health Organization. 2010; WHO/HTM/NTD/GBUI/2010: ISBN 978 92 4 159913 9.
11. Dhivya S, Padma W, Santhini E. Wound dressings—a review. BioMedicine. 2015; 5(4):22.
12. Gainza G, Villullas S, Pedraz J L, Hernandez R M, Igartua M. Advances in drug delivery systems (DDSs) to release growth factors for wound healing and skin regeneration. Nanomedicine: nanotechnology, biology, and medicine. 2015; 11(6):1551-73.
13. Mahmoud A A, Salama A H. Norfloxacin-loaded collagen/chitosan scaffolds for skin reconstruction: Preparation, evaluation and in-vivo wound healing assessment. European Journal of Pharmaceutical Sciences. 2016; 83:155-65.
14. Catanzano O, D'Esposito V, Acierno 5, Ambrosio M R, De Caro C, Avagliano C, et al. Alginate-hyaluronan composite hydrogels accelerate wound healing process. Carbohydrate Polymers. 2015; 131:407-14.
15. Fan L, Yang H, Yang J, Peng M, Hu J. Preparation and characterization of chitosan/gelatin/PVA hydrogel for wound dressings. Carbohydrate Polymers. 2016; 146: 427-34.
16. Atala A. Regenerative medicine strategies. Journal of Pediatric Surgery. 2012; 47:17-28.
17. Aramwit P, Siritientong T, Srichana T. Potential applications of silk sericin, a natural protein from textile industry by-products. Waste Management & Research. 2011; 30(3):217-24.
18. Nishida A, Yamada M, Kanazawa T, Takashima Y, Ouchi K, Okada H. Sustained-release of protein from biodegradable sericin film, gel and spong. International Journal of Pharmaceutics. 2011; 407:44-52.

19. Chlapanidas T, Farago S, Lucconi G, Perteghella S, Galuzzi M, Mantelli M, et al. Sericins exhibit ROS-scavenging, anti-tyrosinase, anti-elastase, and in vitro immunomodulatory activities. Int J Biol Macromol. 2013; 58:47-56.
20. Kaur J, Rajkhowa R, Tsuzuki T, Millington K, Zhang J, Wang X. Photoprotection by silk cocoons. Biomacromolecules. 2013; 14(10):3660-7.
21. Berardesca E, Ardigo M, Cameli N, Mariano M, Agozzino M, Matts P J. Randomized, double-blinded, vehicle-controlled, split-face study to evaluate the effects of topical application of a Gold Silk Sericin/Niacinamide/Signaline complex on biophysical parameters related to skin ageing. International journal of cosmetic science. 2015; 37(6):606-12.
22. Ohnishi K, Murakami M, Morikawa M, Yamaguchi A. Effect of the silk protein sericin on cryopreserved rat islets. Journal of hepato-biliary-pancreatic sciences. 2012; 19(4):354-60.
23. Morikawa M, Kimura T, Murakami M, Katayama K, Terada S, Yamaguchi A. Rat islet culture in serum-free medium containing silk protein sericin. Journal of hepato-biliary-pancreatic surgery. 2009; 16(2):223-8.
24. Wang Z, Zhang Y, Zhang J, Huang L, Liu J, Li Y, et al. Exploring natural silk protein sericin for regenerative medicine: an injectable, photoluminescent, cell-adhesive 3D hydrogel. Scientific Reports. 2014; 4:7064:1-11.
25. Song Y, Zhang C, Zhang J, Sun N, Huang K, Li H, et al. An injectable silk sericin hydrogel promotes cardiac functional recovery after ischemic myocardial infarction. Acta Biomaterialia.
26. Chen L, Hu J, Ran J, Shen X, Tong H. A novel nanocomposite for bone tissue engineering based on chitosan-silk sericin/hydroxyapatite: biomimetic synthesis and its cytocompatibility. RSC Advances. 2015; 5(69): 56410-22.
27. Kundu B, Kundu S C. Silk sericin/polyacrylamide in situ forming hydrogels for dermal reconstruction. Biomaterials. 2012; 33(30):7456-67.
28. Khampieng T, Aramwit P, Supaphol P. Silk sericin loaded alginate nanoparticles: Preparation and anti-inflammatory efficacy. International Journal of Biological Macromolecules. 2015; 80:636-43.
29. Shi L, Yang N, Zhang H, Chen L, Tao L, Wei Y, et al. A novel poly(γ-glutamic acid)/silk-sericin hydrogel for wound dressing: Synthesis, characterization and biological evaluation. Materials Science and Engineering: C. 2015; 48:533-40.
30. Almeida L R, Martins A R, Fernandes E M, Oliveira M B, Correlo V M, Pashkuleva I, et al. New biotextiles for tissue engineering: Development, characterization and in vitro cellular viability. Acta Biomaterialia. 2013; 9:8167-81.
31. Rahimi R, Ochoa M, Parupudi T, Zhao X, Yazdi I K, Dokmeci M R, et al. A low-cost flexible pH sensor array for wound assessment. Sensors and Actuators B: Chemical. 2016; 229:609-17.
32. Ramos Ó L, Reinas I, Silva S I, Fernandes J C, Cerqueira M A, Pereira R N, et al. Effect of whey protein purity and glycerol content upon physical properties of edible films manufactured therefrom. Food Hydrocolloids. 2013; 30(1):110-22.
33. Ribeiro V P, Almeida L R, Martins A R, Pashkuleva I, Marques A P, Ribeiro A S, et al. Influence of different surface modification treatments on silk biotextilesfor tissue engineering applications. Journal of Biomedical Material Research Part B.00B: 000-000.
34. Yan L-P, Silva-Correia J, Oliveira M B, Vilela C, Pereira H, Sousa R A, et al. Bilayered silk/silk-nanoCaP scaffolds for osteochondral tissue engineering: In vitro and in vivo assessment of biological performance Acta Biomaterialia. 2015; 12:227-41.

The invention claimed is:

1. A hydrogel comprising:
    at least 4% (w/v) of an enzymatically cross-linked silk sericin,
    wherein the silk sericin is enzymatically cross-linked by an enzyme complex selected from the group consisting of: horseradish peroxidase and hydrogen peroxide, laccase, transglutaminase, and mixtures thereof;
    wherein a cross-section of said hydrogel has pores with a diameter between 50-100 μm, and;
    wherein the hydrogel is suitable for medicinal applications, veterinary applications, cosmetic applications or as an in vitro model for cell culture studies.

2. The hydrogel of claim 1, wherein the hydrogel comprises at least 7.5% (w/v) of silk sericin.

3. The hydrogel of claim 1, comprising 4-20% (w/v) of an enzymatically cross-linked silk sericin.

4. The hydrogel of claim 1, comprising 6-7.5% (w/v) of an enzymatically cross-linked silk sericin.

5. The hydrogel of claim 1, wherein the silk sericin is enzymatically cross-linked by horseradish peroxidase and hydrogen peroxide for 10 seconds-5 minutes.

6. The hydrogel of claim 1, wherein the silk sericin is enzymatically cross-linked with 0.1-0.6% (w/v) of horseradish peroxidase and 0.15-0.4% (v/v) of hydrogen peroxide.

7. The hydrogel of claim 1, wherein the silk sericin has a molecular weight of 150-400 kDa.

8. The hydrogel of claim 1, wherein said hydrogel has an antioxidant activity of 0.03-0.05 eq [Asc. Ac.]g/L)/g.

9. The hydrogel of claim 1, further comprising a biological active agent, a therapeutic agent, an additive, a pharmaceutically acceptable excipient, a pharmaceutically acceptable carrier, and mixtures thereof.

10. The hydrogel of claim 9, wherein the additive is a surfactant selected from the following list: polysorbates, cationic molecules or polymers, and mixtures thereof.

11. The hydrogel of claim 9, wherein the additive is polysorbate 20, polysorbate 80 or poly-lysine.

12. The hydrogel of claim 9, wherein the biological active agent or the therapeutic agent is selected from the following list: antibiotic, coagulation agent, cell, stem cell, ligand, growth factor, platelet, and mixtures thereof.

13. The hydrogel of claim 12, wherein the antibiotic is vancomycin, streptomycin, ciprofloxacin, or mixtures thereof.

14. The hydrogel of claim 12, wherein the coagulation agent is thrombin or calcium.

15. The hydrogel of claim 1, wherein the hydrogel is transparent.

16. The hydrogel of claim 1, wherein the hydrogel is an injectable hydrogel or a topical hydrogel.

17. An adhesive or a patch comprising the hydrogel of claim 1.

18. A method for producing the hydrogel of claim 1, comprising the following steps:
    extracting silk sericin by immersing cocoons in water, at 100° C. for 40-60 min, in a ratio of 1-3% weight cocoons/volume of water;
    filtering the silk sericin;
    concentrating the silk sericin to at least 4% (w/v);

preparing the hydrogel by adding 0.2% (w/v) of horseradish peroxidase, 0.3% (v/v) hydrogen peroxide and at least 4% (w/v) of silk sericin to water to form a mixture; and mixing the mixture for at least 10 seconds.

\* \* \* \* \*